(12) United States Patent
Hernandez et al.

(10) Patent No.: US 11,432,814 B2
(45) Date of Patent: Sep. 6, 2022

(54) DEVICES, SYSTEMS, AND METHODS FOR SUTURE MANAGEMENT

(71) Applicant: Medos International Sàrl, Le Locle (CH)

(72) Inventors: Joseph Hernandez, Sandwich, MA (US); Benjamin Cleveland, Bellingham, MA (US); Meghan Vento, Raynham, MA (US)

(73) Assignee: Medos International Sarl, Le Locle (CH)

( * ) Notice: Subject to any disclaimer, the term of this patent is extended or adjusted under 35 U.S.C. 154(b) by 160 days.

(21) Appl. No.: 16/829,623

(22) Filed: Mar. 25, 2020

(65) Prior Publication Data

US 2021/0007730 A1    Jan. 14, 2021

Related U.S. Application Data

(60) Continuation of application No. 15/347,244, filed on Nov. 9, 2016, now Pat. No. 10,624,625, which is a
(Continued)

(51) Int. Cl.
*A61B 17/04* (2006.01)
*A61B 17/34* (2006.01)
(Continued)

(52) U.S. Cl.
CPC ...... *A61B 17/0401* (2013.01); *A61B 17/0482* (2013.01); *A61B 17/0483* (2013.01);
(Continued)

(58) Field of Classification Search
CPC ............ A61B 17/0401; A61B 17/0482; A61B 17/0483; A61B 17/0485; A61B 17/06061;
(Continued)

(56) References Cited

U.S. PATENT DOCUMENTS 5,520,696 A * 5/1996 Wenstrom, Jr. .... A61B 17/0401
606/104
5,522,845 A  6/1996 Wenstrom, Jr.
(Continued)

FOREIGN PATENT DOCUMENTS

CN   102551821 A   7/2012
CN   102551824 A   7/2012
(Continued)

OTHER PUBLICATIONS

Indian Examination Report for Application No. 409/DEL/2014, dated Oct. 27, 2020 (5 pages).
(Continued)

*Primary Examiner* — Ashley L Fishback
*Assistant Examiner* — Christian D Knauss (57) ABSTRACT

Devices, systems, and methods are provided for managing suture filament during a tissue repair procedure. One exemplary embodiment of an anchor insertion tool includes a handle, an elongate shaft extending distally from the handle, and a ring disposed around the elongate shaft. The ring can be configured to slide along a length of the shaft, and can be configured to engage a filament extending from an anchor removably coupled to the shaft's distal end during a suture anchor insertion procedure. In some embodiments, the ring can include one or more slots for receiving a filament and maintaining a tension applied to the filament. The ring can also include features that prevent it from rotating with respect to the shaft, such as a boss formed on a ring's central opening that engages a slot formed in the shaft. Other devices, systems, and methods for suture anchor insertion are also provided.

7 Claims, 7 Drawing Sheets

Related U.S. Application Data division of application No. 13/869,625, filed on Apr. 24, 2013, now Pat. No. 9,510,820.

(51) Int. Cl.
*A61B 17/06* (2006.01)
*A61F 2/08* (2006.01)

(52) U.S. Cl.
CPC ...... *A61B 17/0485* (2013.01); *A61B 17/3417* (2013.01); *A61B 17/3474* (2013.01); *A61B 2017/044* (2013.01); *A61B 2017/0409* (2013.01); *A61B 2017/0445* (2013.01); *A61B 2017/06147* (2013.01); *A61B 2017/06152* (2013.01); *A61F 2002/0841* (2013.01); *A61F 2002/0852* (2013.01)

(58) Field of Classification Search
CPC ........ A61B 17/3417; A61B 2017/0409; A61B 2017/044; A61B 2017/0445; A61B 2017/0496; A61B 2017/06142; A61B 2017/06147
See application file for complete search history.

(56) References Cited

U.S. PATENT DOCUMENTS

| | | | |
|---|---|---|---|
| 5,584,860 A * | 12/1996 | Goble | A61B 17/0401 606/232 |
| 5,697,931 A | 12/1997 | Thompson | |
| 5,752,963 A * | 5/1998 | Allard | A61B 17/0401 606/232 |
| 5,989,252 A * | 11/1999 | Fumex | A61B 17/0401 606/232 |
| 7,122,039 B2 * | 10/2006 | Chu | A61B 17/0482 606/144 |
| 7,654,321 B2 | 2/2010 | Zazovsky et al. | |
| 7,758,598 B2 | 7/2010 | Conlon et al. | |
| 7,850,700 B2 | 12/2010 | Sakura | |
| 8,162,960 B2 | 4/2012 | Manzo | |
| 8,162,978 B2 | 4/2012 | Lombardo et al. | |
| 8,197,511 B2 | 6/2012 | Miller et al. | |
| 8,535,350 B2 | 9/2013 | Lizardi et al. | |
| 8,814,905 B2 | 8/2014 | Sengun et al. | |
| 9,510,820 B2 | 12/2016 | Hernandez et al. | |
| 9,532,778 B2 | 1/2017 | Sengun et al. | |
| 10,624,625 B2 | 4/2020 | Hernandez et al. | |
| 2005/0065535 A1 * | 3/2005 | Morris | A61B 17/0469 606/148 |
| 2005/0228448 A1 | 10/2005 | Li | |
| 2007/0213730 A1 | 9/2007 | Martinek et al. | |
| 2010/0016869 A1 * | 1/2010 | Paulk | A61B 17/0401 606/232 |
| 2010/0069923 A1 | 3/2010 | Nguyen et al. | |
| 2010/0161042 A1 | 6/2010 | Maisano et al. | |
| 2010/0198235 A1 | 8/2010 | Pierce et al. | |
| 2010/0305576 A1 | 12/2010 | Ferguson et al. | |
| 2012/0053623 A1 | 3/2012 | Sojka et al. | |
| 2012/0053629 A1 * | 3/2012 | Reiser | A61B 17/0401 606/232 |
| 2013/0325064 A1 | 12/2013 | Lizardi et al. | |
| 2014/0005720 A1 | 1/2014 | Hirotsuka et al. | |
| 2014/0228866 A1 | 8/2014 | Fallin et al. | |
| 2014/0324099 A1 | 10/2014 | Hernandez et al. | |
| 2017/0000479 A1 | 1/2017 | Sengun et al. | |
| 2017/0055976 A1 | 3/2017 | Hernandez et al. | |

FOREIGN PATENT DOCUMENTS

| | | |
|---|---|---|
| CN | 103027723 A | 4/2013 |
| JP | 2004097849 A | 4/2004 |
| WO | 97/27799 A1 | 8/1997 |
| WO | 2003/090627 A2 | 11/2003 |
| WO | 2013/003746 A1 | 1/2013 |

OTHER PUBLICATIONS

**Chinese Office Action for Application No. 201410168442.7, dated Aug. 23, 2017 (15 pages).
**European Search Report for Application No. 14165844.3, dated February 2, 2015. (7 pages).
U.S. Appl. No. 13/869,625, filed Apr. 24 2013, Devices, Systems, and Methods.
U.S. Appl. No. 15/347,244, filed Nov. 9, 2016, Devices, Systems and Methods for Suture Management.

* cited by examiner

DEVICES, SYSTEMS, AND METHODS FOR SUTURE MANAGEMENT

CROSS REFERENCE TO RELATED APPLICATION

The present application is a continuation of and claims priority to U.S. application Ser. No. 15/347,244, filed Nov. 9, 2016, and entitled "Devices, Systems, and Methods for Suture Management," which is a divisional of and claims priority to U.S. application Ser. No. 13/869,625, filed Apr. 24, 2013, and entitled "Devices, Systems, and Methods for Suture Management," and which issued as U.S. Pat. No. 9,510,820 on Dec. 6, 2016, the contents of each which is hereby incorporated by reference in their entireties.

FIELD

The present disclosure relates to devices, systems, and methods for securing soft tissue to bone, and more particularly relates to managing suture filament during a tissue repair procedure.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone.

One common procedure used in tissue repair involves coupling a suture filament associated with a surgical implant, such as an anchor, staple, or tack, to the detached tissue. The surgical implant can be disposed proximate to a desired location for the detached tissue, such as in a bone, and then tension can be applied to the suture filament to draw the detached tissue toward the surgical implant. In exemplary embodiments of a repair procedure, no knots are tied by the surgeon to couple the suture filament to the detached tissue or to move the detached tissue to the desired location. Once the tissue arrives at the desired location, it can be secured at the location using any number of techniques known to those skilled in the art.

Tissue repair procedures such as the one described above can be performed using minimally invasive surgical techniques, such as endoscopies and laparoscopies to minimize the amount of recovery time, pain, and surgery-related complications. A trocar is disposed at the surgical site and the suture filament and surgical implant are disposed therethrough to perform the repair procedure. A number of complications exist, however, with the current tools and techniques used in such repairs, including complications related to managing suture filament during the course of the repair.

For example, current tools require that a long length of suture filament be used to perform the repair. Typically the filament extends a substantial length outside of the trocar, for instance at least halfway up a shaft of an insertion tool, or even further. Additionally, it can be difficult to keep track of filament being used during the procedure. Each suture filament typically includes two terminal ends that extend out of the trocar, and when multiple filaments are used during a repair procedure, it can be challenging to keep track of the various ends of the filaments. Challenges further escalate when tension is applied to one or more of the ends of the suture filaments. Surgeons find it difficult to apply and retain tension in one suture filament while attempting to manipulate and tension other suture filaments.

Another complication presently faced in view of existing tools and techniques is undesirable wrapping of the filaments that can occur when inserting a surgical implant into bone. As an insertion tool is rotated to implant the surgical implant in bone, the filaments associated with that implant can undesirably wrap around the shaft of the insertion tool. This is particularly troublesome when the wrapping occurs below an access port of a trocar. The filaments and tool can become tangled and difficult to manage during and after the insertion, and when the wrapping occurs below the access port, it is difficult for the surgeon to access the tangled filaments to try and loosen it away from the shaft.

Accordingly, it would be desirable to provide devices, systems, and methods that assist in managing suture filament during endoscopic and laparoscopic tissue repair procedures.

SUMMARY

Devices, systems, and methods are generally provided for managing suture filament during a tissue repair procedure. In one exemplary embodiment, a suture anchor insertion tool is provided and includes a handle, an elongate shaft extending distally from the handle, and a ring disposed around the elongate shaft and slidable along a length of the shaft. The shaft can have a slot formed along at least a portion of its length, as well as a cannulated distal end that is in communication with the slot. The distal end can be configured to engage a suture anchor. The ring can include a central opening, and the ring can be configured to engage a trailing end of a suture filament extending from the slot of the shaft during a suture anchor insertion procedure.

The ring can include at least one slot extending from a proximal surface of the ring and toward a distal surface of the ring. The slot can be configured to receive a suture filament. In some embodiments the ring can include multiple slots disposed approximately equidistantly around a circumference of the ring. The handle of the tool can also include a component that has a slot formed in it. The slot can be configured to receive a filament extending into the handle from a location distal of the slot.

The ring can be non-rotatably coupled to the elongate shaft. For instance, the ring can include a boss formed in its central opening, and the boss can be configured to engage the slot of the shaft when the ring slides along a length of the shaft. The engagement of the boss within the slot can prevent the ring from rotating with respect to the shaft.

In an exemplary embodiment of a suture anchor insertion assembly, the assembly provided includes a handle, an elongate shaft extending distally from the handle, a ring slidably disposed around the elongate shaft, and a suture anchor removably and replaceably coupled to a distal end of the shaft. The ring can be configured to engage a suture filament extending from the anchor. The ring can also be configured to slide relative to the elongate shaft to apply tension to the suture filament as the suture anchor is driven into bone.

The assembly can also include a suture filament coupled to the suture anchor, the filament extending along at least a portion of a slot formed in the elongate shaft, and extending through a central opening of the ring. Further, the assembly can include a threader. The threader can have a distal portion disposed distal of the suture anchor, a proximal portion disposed proximal of the ring, and a flexible intermediate portion disposed therebetween. The distal portion can be configured to receive a suture filament for loading onto the suture anchor. The proximal portion can include a handle portion to assist in pulling a suture loaded on the distal portion through the suture anchor. The assembly can also include a filament extending from the handle, through the elongate shaft to the shaft's distal end, and back through the elongate shaft to the handle. The filament can be configured to removably couple the anchor to the distal end of the elongate shaft.

The ring can include at least one slot extending from a proximal surface of the ring and toward a distal surface of the ring. The slot can be configured to receive a suture filament. In some embodiments the ring can include multiple slots disposed approximately equidistantly around a circumference of the ring. Further, the ring can be non-rotatably coupled to the elongate shaft. In some embodiments the ring can include a boss that extends into a slot of the elongate shaft to prevent rotation of the ring relative to the shaft.

In other aspects, a method for repairing tissue is provided and includes inserting a suture anchor removably and replaceably coupled to a distal end of an inserter shaft through a cannula to position the suture anchor adjacent to an implant site. The suture anchor can have a suture filament associated with it, the filament extending proximally from the anchor and through the inserter shaft. The shaft can have a ring slidably disposed around it and coupled to the suture filament such that as the anchor moves toward the implant site, the ring slides relative to the insert shaft and a distance between the anchor and the ring increases.

As the anchor moves toward the implant site, the ring can abut a face of the cannula. In some embodiments, the method can further include inserting the suture filament into a slot of the ring to maintain a tension applied to the suture filament. The method can also include rotating the inserter shaft to insert the suture anchor into bone. While the inserter shaft is rotated, the ring can guide a trailing portion of the suture filament through a slot formed in the inserter shaft.

The filament can be loaded onto the anchor using any number of techniques. In some embodiments a threader having a proximal portion, a distal portion, and an intermediate portion can be used. The method can include loading the suture filament onto a distal portion of the threader when the distal portion is located distal of the suture anchor. The intermediate portion can extend through the suture anchor, and the proximal portion can be located proximal of the suture anchor, adjacent to the ring. The proximal portion of the threader can be pulled proximally along the shaft, away from the ring. This, in turn, can advance the distal portion of the threader, and thus the suture filament loaded thereon, through the suture anchor and through the ring.

Still further, the method can include decoupling the suture anchor from the inserter shaft, and removing the inserter shaft from the implant site. As the shaft is removed from the implant site, the ring can guide a trailing portion of the suture filament through a slot formed in the inserter shaft. In some embodiments, a second suture filament extending distally from the handle and to a distal end of the anchor can be released to decouple the anchor from the inserter shaft.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Additionally, to the extent that linear or circular dimensions are used in the description of the disclosed devices, systems, and methods, such dimensions are not intended to limit the types of shapes that can be used in conjunction with such devices, systems, and methods. A person skilled in the art will recognize that an equivalent to such linear and circular dimensions can easily be determined for any geometric shape. Further, a number of terms may be used throughout the disclosure interchangeably but will be understood by a person skilled in the art. By way of non-limiting examples, terms such as "suture" and "filament," "device" and "tool," and "system" and "assembly" may be used interchangeably.

The present disclosure is generally directed to anchor insertion devices having features that assist in managing suture used in conjunction with surgical implants, such as suture anchors, to perform tissue repair procedures. In exemplary embodiments one such feature is a ring disposed around a shaft of an anchor insertion device. As described herein, the ring can be configured to manage suture in a variety of ways. In one instance, it manages suture by sliding with respect to the shaft and engaging suture filament disposed between the ring and shaft. In doing so, the ring guides the filament and can prevent it from tangling when the shaft is moved laterally with respect to the ring. The ring can also prevent the filament from tangling when the shaft is rotated, which can occur when the surgical implant is being inserted into bone. The ring can also be adapted to help manage suture filament while the filament is being manipulated by a surgeon to secure soft tissue at a desired location. For example, one or more slots can be formed in the ring and can be configured to receive and hold filament, thereby freeing a surgeon's hands to perform other functions while tension applied to the filament is retained by virtue of the slot.

Figure 1A:
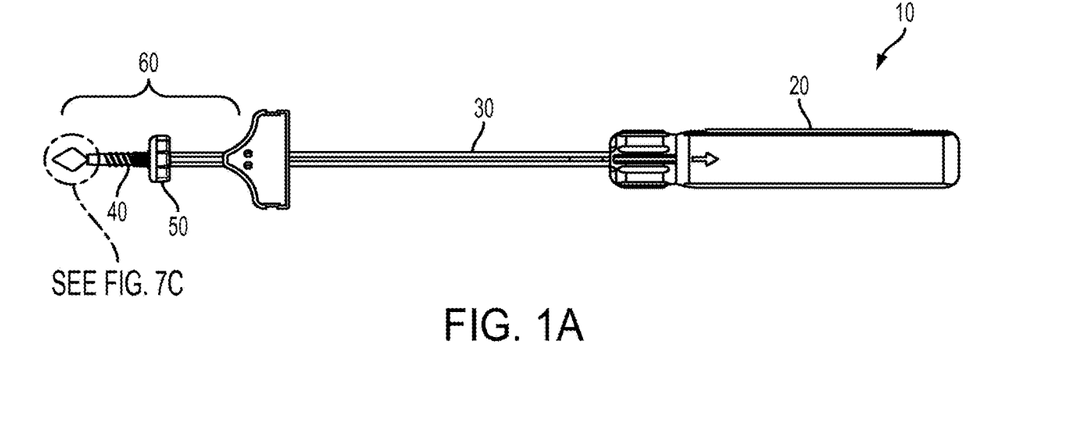
FIG. 1A is a top view of one exemplary embodiment of a suture anchor insertion device.
Figure 1B:
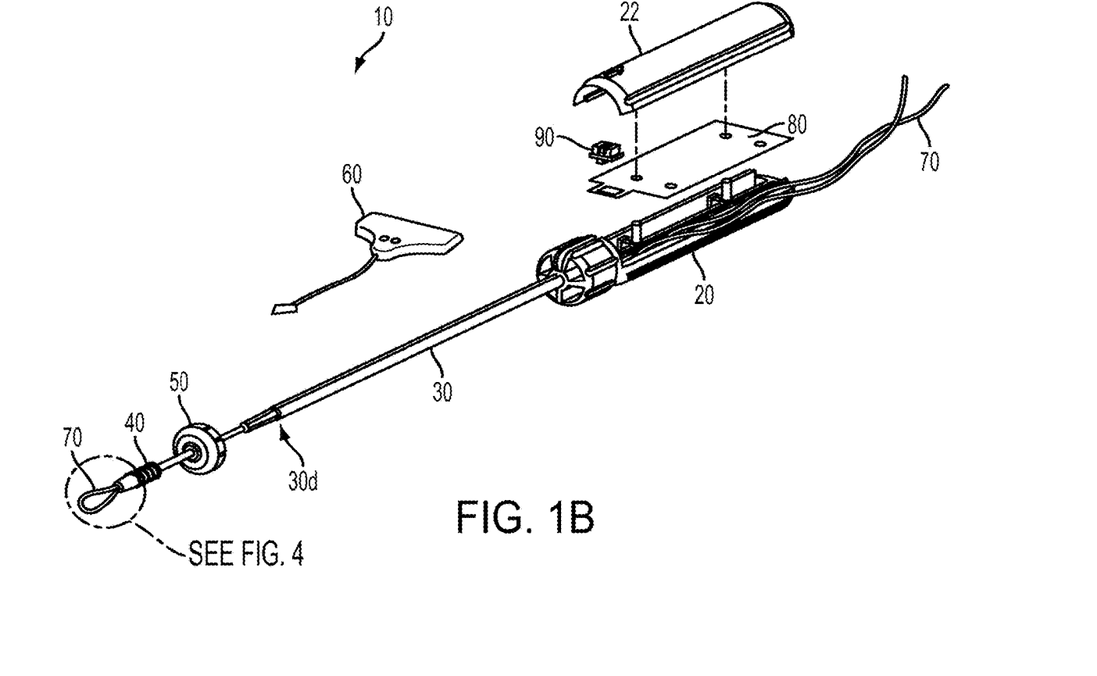
FIG. 1B is a perspective exploded view of the device of FIG. 1A.

While a person skilled in the art will recognize that features that assist in managing suture like a ring can be incorporated into any number of insertion tool and device designs, one exemplary embodiment of such a device 10 is provided in FIGS. 1A and 1B. As shown, the device 10 generally includes a handle 20 and a shaft 30 having a distal end 30d configured to engage a surgical implant, such as an anchor 40. A ring 50 can be slidably disposed around the shaft 30 and can assist in managing suture filament that extends proximally from the anchor 40. In the illustrated embodiment, a threader 60 is provided to couple suture filament to the anchor 40 for use in the tissue repair. A stay suture 70 is also provided to maintain the anchor 40 in engagement with the shaft 30 while the anchor is inserted to a surgical site. As shown, the stay suture 70 extends from handle 20, to a distal end of the anchor 40, and back to the handle 20.

The handle 20 can also include one or more features for suture filament storage. As shown, the handle includes a suture storage card 80, around which the stay suture 70 can be disposed. The card 80 can be accessed by opening a handle door 22 and the card 80 can be removed from the handle 20 to allow the stay suture 70 to be disconnected from the handle 20. When the stay suture 70 is released, the anchor 40 can be detached from the shaft 30 and the shaft 30 can be removed from the surgical site. In some embodiments a gripper 90 can be associated with the card 80 and can be used to selectively hold the stay suture 70. Each of the components of the device 10 is described in more detail below.

Figure 2A:
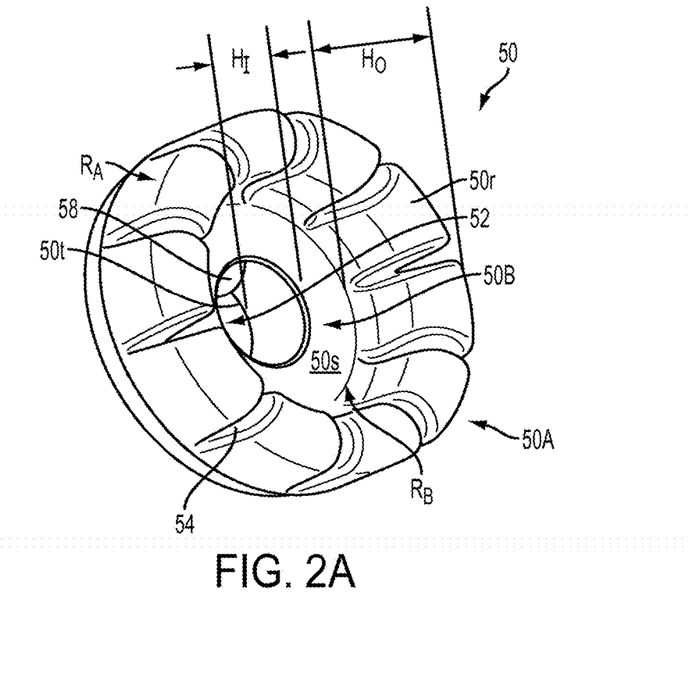
FIG. 2A is a perspective view of a suture management ring of the device of FIG. 1A.
Figure 2B:
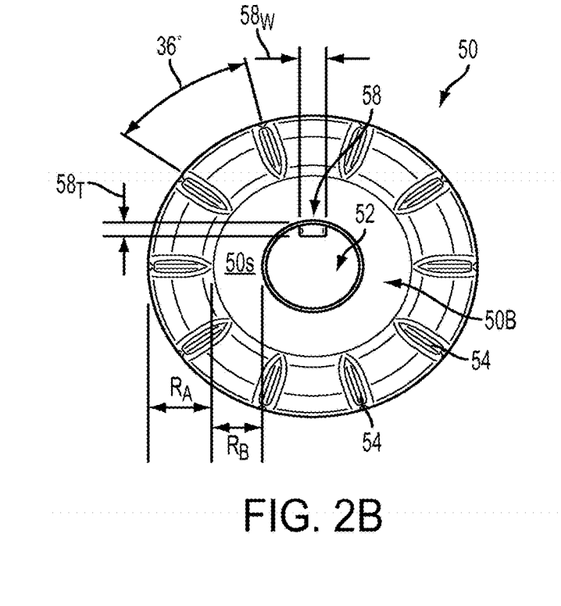
FIG. 2B is a top view of the suture management ring of FIG. 2A.

FIGS. 2A and 2B illustrate ring 50 in more detail. In the illustrated embodiment, the ring 50 is generally circular in shape and has a central opening 52 formed therein. The central opening 52 can be sized and shaped to slide closely along a length of the shaft 30 of the insertion device 10, and in the illustrated embodiment is substantially circular. As shown, an outer portion 50A of the ring 50 is raised above a surface 50s of an inner portion 50B of the ring 50. Accordingly, a height $H_O$ of the outer portion 50A can be greater than a height $H_I$ of the inner portion 50B. In other embodiments, the ring 50 can have a substantially uniform height.

In some embodiments, the ring 50 can include one or more features to help a surgeon manage multiple ends of suture filament(s) at a time. In the illustrated embodiment the features are in the form of a plurality of slots 54 formed in the outer portion 50A. As shown, ten slots 54 are formed approximately equidistantly around a circumference of the ring 50, i.e., approximately 36 degrees apart, although any number of slots, including just a single slot, can be formed in the ring 50, and the slots do not have to be equally spaced around the circumference of the ring 50. The slots 54 can be configured to receive and retain suture filament, and can also be adapted to maintain a tension applied to a filament.

Figure 2C:
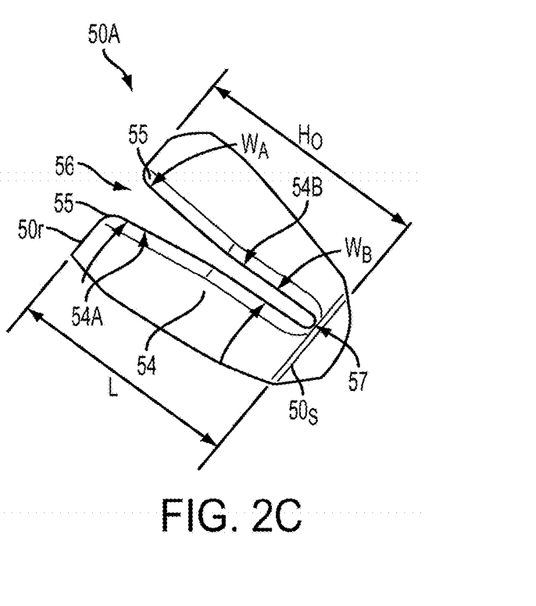
FIG. 2C a side view of one slot of the suture management ring of FIG. 2A.

In some embodiments a width of an opening 56 of a slot 54 can be substantially uniform throughout, but as shown in FIG. 2C, in some exemplary embodiments a width $W_A$ of the slot 54 at an opening end 54A can be larger than a width $W_B$ at a closed end 54B. Such a configuration can make it easier to initially insert filament into the slot 54 and can more easily allow tension applied to the filament to be retained by disposing the filament in the slot 54 at the smaller width $W_B$. The slot 54 can also included rounded or chamfered edges 55 at the top of the opening 56, and a rounded bottom portion 57, to reduce the risk of the filament chafing or fraying.

The ring 50 can also include one or more features to help prevent the ring 50 from rotating with respect to an insertion tool shaft around which it is disposed. In the illustrated embodiment the ring 50 includes a boss 58 formed on a circumference of the central opening 52. The boss 58 is adapted to be seated within a slot formed in the shaft 30 of the tool 10 such that edges of the boss 58 can slide along, or at least be proximate to, edges of the shaft slot. As shown, the boss 58 has a curved outer surface, a substantially rectangular cross-section, and a width that is complementary to a width of the slot of the shaft 30.

In general, the size and shape of the ring 50 can depend on a number of different factors including the sizes and shapes of other components with which the ring is used, and the type of procedure in which it is used. Accordingly, while the ring 50 and its central opening 52 are shown as being substantially circular, either can have a different shape without departing from the spirit of the present disclosure. In some embodiments a diameter of the ring 50 can be in the range of about 0.7 centimeters to 6 centimeters, and in one embodiment is about 1.5 centimeters, while a diameter of the central opening 52 can be in the range of about 2 millimeters to 12 millimeters, and in one embodiment is about 4.5 millimeters. In some embodiments the height $H_O$ of the outer portion 50A can be in the range of about 3 millimeters to 20 millimeters, and in one embodiment is about 6.3 millimeters, while the height $H_I$ of the inner portion 50B can be in the range of about 1 millimeter to 5 millimeters, and in one embodiment is about 2.5 millimeters. Further, while a radius of the outer portion 50A and a radius of the inner portion 50B can have different sizes, in the illustrated embodiment a radius $R_A$ of the outer portion is substantially similar to a radius $R_B$ of the inner portion. The radius $R_A$ and the radius $R_B$ can be in the range of about 1 millimeter to 10 millimeters, and in one embodiment each is about 3.1 millimeters.

Likewise, the sizes and shapes of features of the ring 50, such as its slots 54 and boss 58, can depend on factors such as the sizes and shapes of other components with which the ring is used, and the type of procedure in which it is used. In the illustrated embodiment, a length L of each slot 54 can be approximately equal to the distance between a top surface 50r of the inner portion 50A and a top surface 50s of the outer portion 50B, and can be in the range of about 1 millimeter to 10 millimeters. In one embodiment the length L is about 3.8 millimeters. A width $W_B$ of the slot 54 at the lower height can be in the range of about 0.1 millimeters to about 1.0 millimeters, and in one embodiment is about 0.3 millimeters, and a width $W_A$ of the slot 54 at the higher height can be in the range of about 0.1 millimeters to about 2.0 millimeters, and in one embodiment is about 0.8 millimeters. A person skilled in the art will recognize that each slot can have different dimensions and that some slots can be configured for use with differently sized sutures. A width $58_W$ of the boss 58 can be in the range of about 0.5 millimeters to 4 millimeters, and in one embodiment is about 1.2 millimeters. A length of the boss can be defined by the portion that extends between the surface 50s of the ring 50 and a terminal distal end 50t, and can be in the range of about 1 millimeter to 6 millimeters, and in one embodiment is about 2.5 millimeters. A thickness 58T of the boss 58 can be in the range of about 0.1 millimeters to 2 millimeters, and in one embodiment is about 0.6 millimeters.

The ring 50 can be made from any number of materials, including, by way of non-limiting example, polymers such as elastomers. In one exemplary embodiment the ring 50 is made of polyisoprene. Factors that similarly affect the size of the ring can also affect the type of material used to form the ring, including the materials of other components, and the type of procedure in which the ring is used.

Figure 3A:
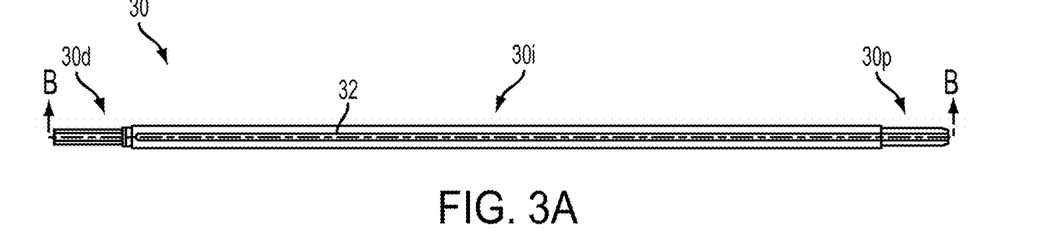
FIG. 3A is a side view of an elongate shaft of the device of FIG. 1A.
Figure 3B:
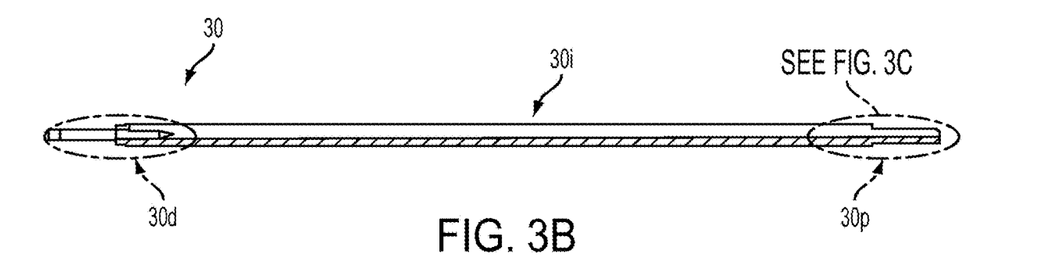
FIG. 3B is a cross-sectional side view of the elongate shaft of FIG. 3A.

The shaft 30 around which the ring 50 can be disposed can have a variety of configurations, but as shown in FIGS. 3A and 3B, it is generally elongate, it has a proximal end 30p configured to mate with a handle, and a distal end 30d configured to mate with an anchor to be implanted. At least a portion of the shaft 30 can include an opening for receiving suture filament. In the illustrated embodiment, the distal end 30d is cannulated and a slot 32 is formed in a sidewall and extends from a location proximate to the distal end 30d, through an intermediate portion 30i of the shaft 30, and through the proximal end 30p. The distal end of the slot 32 can communicate with the cannulation in the distal end 30d of the shaft 30, thereby allowing a filament to extend through the cannulated distal end 30d and extend along the length of the slot 32. In other embodiments the slot 32 may terminate prior to the proximal end 30p.

Figure 3C:
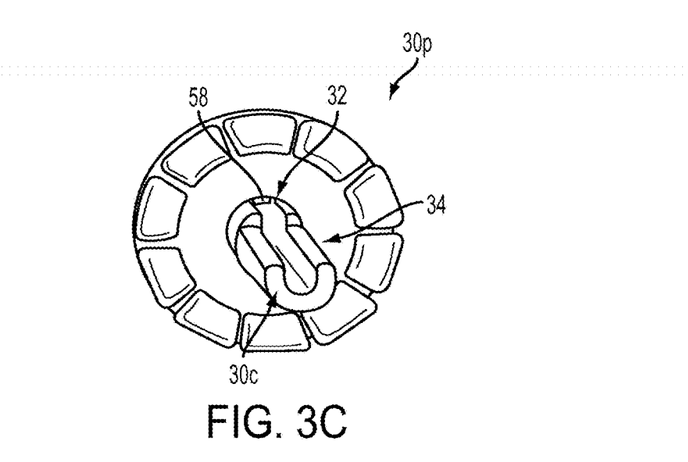
FIG. 3C is a top perspective view of the suture management ring of FIG. 2A coupled to the elongate shaft of FIG. 3A.
Figure 3D:
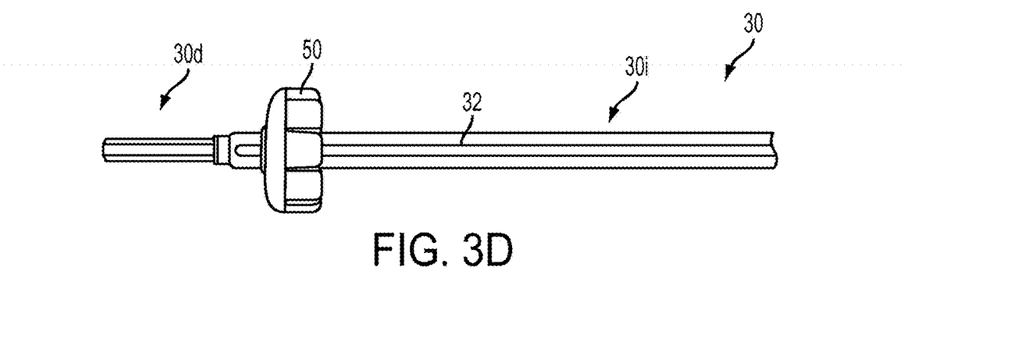
FIG. 3D is a side perspective view of the suture management ring and elongate shaft of FIG. 3C.

As shown in FIG. 3C, the proximal end 30p can include a reduced diameter or keyed section 34 that is configured to be complementary with a handle portion, such as the handle 20. As a result, the handle 20 and shaft 30 can be securely mated during an insertion procedure. In other embodiments the shaft and handle can be fixedly mated or integrally formed. The intermediate portion 30i can have a substantially uniform thickness with the slot 32 extending through at least a portion thereof. As shown, the slot 32 is formed in a surface of the shaft 30 and extends into a central portion 30c of the shaft 30, forming a substantially U-shaped slot. The boss 58 formed in the ring 50 can extend into and align with the slot 32 to prevent rotation of the ring 50 as it slides from the proximal end 30p (FIG. 3C) and towards the distal end 30d (FIG. 3D). Similar to the proximal end 30p, the distal end 30d can include a reduced diameter portion as compared to the main or intermediate portion 30i. The distal end 30d can be sized to be complementary to a suture anchor, such as the anchor 40.

The size of the shaft 30 and materials from which it is made can depend on factors such as the sizes and shapes of other components with which the shaft is used, and the type of procedure in which it is used. As shown, the shaft 30 is generally cylindrical in shape and has a diameter in the range of about 2 millimeters to 12 millimeters, and in one embodiment is about 4.5 millimeters. A length of the shaft 30 can be in the range of about 18 centimeters to 30 centimeters, and in one embodiment is about 24 centimeters. The shaft 30 can be formed from materials such as biocompatible materials and metals, and in one exemplary embodiment the shaft 30 is formed from stainless steel or titanium.

Figure 4A:
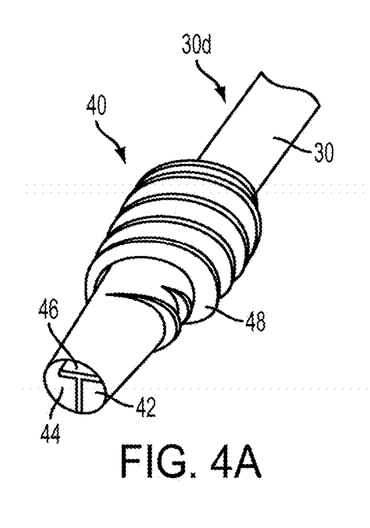
FIG. 4A is a perspective view of an anchor of FIG. 1A.
Figures 4B, 4C:
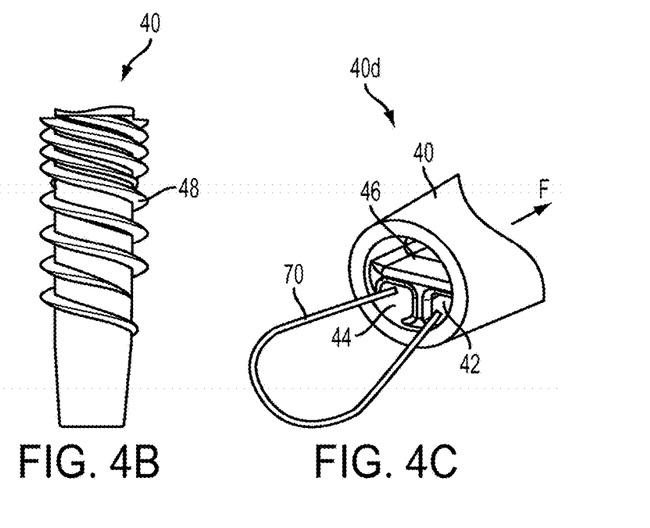
FIG. 4B is a side perspective view of the anchor of FIG. 4A.
FIG. 4C is a perspective view of a distal end of the anchor of FIG. 4A, the anchor having a stay suture filament associated therewith.

The anchor 40 that is removably and replaceably coupled to the distal end 30d of the shaft 30 can have many different configurations. In the embodiment of FIGS. 4A-4C, the anchor 40 is in the form of a cannulated elongate cylindrical member. An outer surface of the anchor 40 can include one or more bone-engaging features, such as threads 48, to assist in implanting the anchor in bone. As shown in FIG. 4C, the anchor 40 includes a plurality of chambers 42, 44, 46 that extend through the anchor 40. In the illustrated embodiment volumes of the first and second chambers 42, 44 are approximately half as large as the volume of the third chamber 46, although any number and size of chambers can be used without departing from the spirit of the present disclosure.

The first and second chambers 42, 44 can be adapted to receive a stay suture 70, and the third chamber 46 of the anchor 40 can be configured to receive operative sutures to be used during a surgical procedure and a threader. The stay suture 70 can secure the anchor 40 to the shaft 30, the operative sutures can be used to secure tissue to bone as part of the surgical procedure, and the threader can be used to pass the operative sutures through the anchor 40. In the illustrated embodiment, the stay suture 70 extends from the handle 20, through the shaft 30, through the first chamber 42, out of the anchor 40, back into the anchor 40 through the second chamber 44, back through the shaft 30, and back into the handle 20. A tension in an approximate direction F can be applied to the stay suture 70 that counteracts gravity, thereby helping hold the anchor 40 on the shaft 30. The tension can be held in the stay suture 70 by components disposed in the handle 20, as discussed below. A person skilled in the art will recognize other ways by which the anchor 40 can be held onto the shaft 30, including but not limited to mechanical and frangible connections between the anchor 40 and the shaft 30, and thus the disclosure of a stay suture in no way limits the way an anchor 40 can be connected to the shaft 30. Further, a person skilled in the art will recognize that other types of surgical implants, including but not limited to staples and tacks, can also be adapted for use in conjunction with the tool 10.

Similar to the other components of the system or assembly, the sizes and materials used to form the anchor can depend, at least in part, on the sizes and shapes of other components with which the anchor is used, and the type of procedure in which it is used. One exemplary, non-limiting embodiment of an anchor that can be used in the disclosed assembly is the Healix Advance Knotless anchor, which is commercially available from DePuy Mitek, Inc., 325 Paramount Drive, Raynham, Mass. 02767.

Likewise, the size and materials used as a stay suture can depend on similar factors. In one exemplary, non-limiting embodiment, the stay suture can be a #2 Orthocord™ filament, which is commercially available from DePuy Mitek, Inc, and can have a length of about 91.4 centimeters. Other filament types, such as Ethibond™ filament, which is commercially available from Ethicon, Inc., Route 22 West, Somerville, N.J. 08876, as well as other sizes, can also be used. In some embodiments, the filament for the stay suture 70 can have a size between about a #5 filament (about 20 gauge to about 21 gauge) and a #5-0 filament (about 35 gauge to 38 gauge) and can have a length in the range of about 35 centimeters to 135 centimeters. The operative filament used to repair the tissue that is disposed through the anchor 40 can have similar characteristics as it pertains to size and material, again depending on the sizes and shapes of other components, and the type of procedure being performed.

Figure 5:
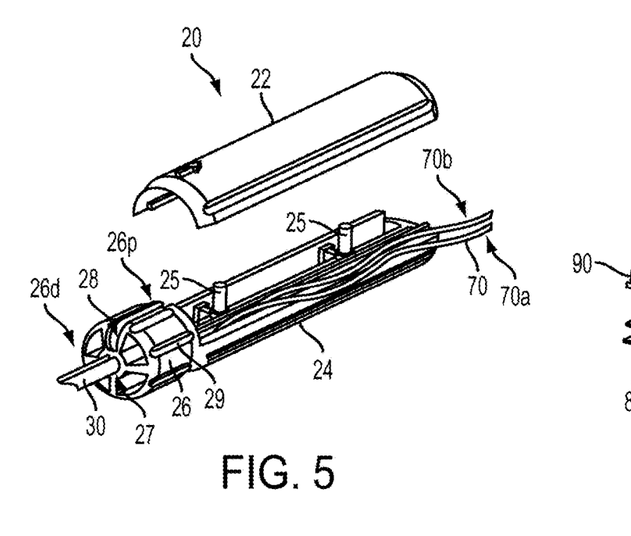
FIG. 5 is a perspective exploded view of a handle of the device of FIG. 1A.

The proximal end 30p of the shaft 30 can be coupled to a handle 30 of the device 10. As shown in FIG. 5, the handle 20 can be a housing having a substantially cylindrical shape and can include a storage chamber 24, a cover or door 22, and a distal knob 26. The distal knob 26 can include an aperture 27 formed therein that is complementary to a shape of the proximal end 30p of the shaft 30. The aperture 27 can extend from a distal end 26d of the knob 26 to a proximal end 26p of the knob 26. The knob 26 can be configured to rotate the shaft 30. A longitudinally-extending slot 28 can optionally be formed in the knob 26. In some embodiments, for instance when there is no aperture 27 that extends fully through the knob 26, the slot 28 can be used to pass a filament from the slot 32 into the storage chamber 24. In such an embodiment, the filament can pass through the slot 28, under the cover 22, and into the storage chamber 24. The knob 26 can also include grooves 29 formed in a surface thereof, which can allow a surgeon to more easily grasp and rotate the knob 26 as desired.

The storage chamber 24 can be configured to store the stay suture 70. Many techniques can be used to store the stay suture 70 within the chamber 24, but in some embodiments a filament storage card 80, such as the one shown in FIG. 6 and described in further detail below, can be used. One or more posts 25 can be formed in the chamber 24 to receive complementary apertures formed in the card 80.

The cover 22 can be detachable from the storage chamber 24. In the illustrated embodiment the cover 22 forms a snap-fit with the storage chamber 24 and a proximal end 26 of the knob 26. Once the cover 22 is detached from the rest of the handle 20, the storage chamber 24 is accessible. Accordingly, the stay suture 70 can be accessed and disconnected from the card 80 so that the anchor 40 and shaft 30 can be separated. A person skilled in the art will recognize a number of other ways by which the cover 22 can be attached to the storage chamber 24 to allow the cover to be opened to access the storage chamber 24, including, by way of non-limiting example, a hinge being formed between the storage chamber 24 and the cover 22, or the cover 22 having a slidable opening that provides access to the storage chamber 24 from the outside. Accordingly, the cover 22 does not have to be fully detached from the chamber 24 to access the chamber 24, but rather must just be opened in some fashion to permit access.

Figure 6:
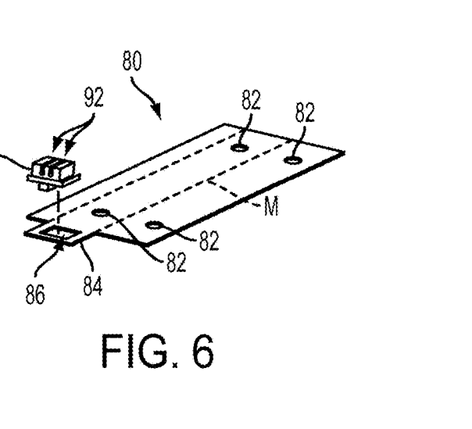
FIG. 6 is a perspective view of a suture management card and suture gripper of the device of FIG. 1A.

One exemplary embodiment of a filament storage card 80 is illustrated in FIG. 6. Like many of the other components described herein, the card 80 can be any number of shapes and sizes. As shown, it is generally configured to fit within the confines of the handle 20, is substantially rectangular, substantially flat, and substantially thin. The card 80 can include one or more apertures 82 formed thereon to allow the card to be stored on posts 25 provided within the handle 20, as shown in FIG. 5. In the illustrated embodiment there are four apertures 82, and the card 80 is designed to be folded along a line M so that each pair of apertures 82 is concentric and disposable on the posts 25.

Optionally, a distal tab 84 can be included as part of the card 80, the tab 84 being configured to hold a filament gripper 90. As shown, an opening 86 is formed in the tab 84 and is configured to receive the gripper 90. The filament gripper 90 can include one or more slots or barrels 92 configured to grasp filament and hold a location of the filament as desired. In the illustrated embodiment the gripper 90 includes two slots 92, each of which is configured to grasp terminal ends 70a, 70b of the stay suture 70. By grasping the stay suture 70, a tension can be maintained therein to adequately hold the anchor 40 on the shaft 30. Excess stay suture 70 can then be stored in the chamber 24 of the handle 20, for instance by wrapping the stay suture 70 in a figure eight pattern around the posts 25 and/or be wrapping it around the card 80. While the card 80 and gripper 90 can be formed of any number of materials, in some exemplary embodiments each is made of a plastic material. In some other embodiments, no card is used and the handle 20 can include other features adapted to receive and apply tension to the stay suture 70.

A threader 60 can be used to pass one or more operative suture filaments through the anchor 40. The threader 60 can be configured to allow for a starting position of a proximal end of a threader to be close to a port of a trocar to allow a suture filament extending from the anchor to be accessed shortly after it extends outside of the port. The additional control afforded by the ring 50 allows for the use of shorter operative filaments, and thus allows the threader 60 to start proximate to the port of a trocar, as described in greater detail below. Additionally, while many threaders are designed to be in two separate parts, the threader 60 of the present disclosure is a singular component.

Figure 7A:
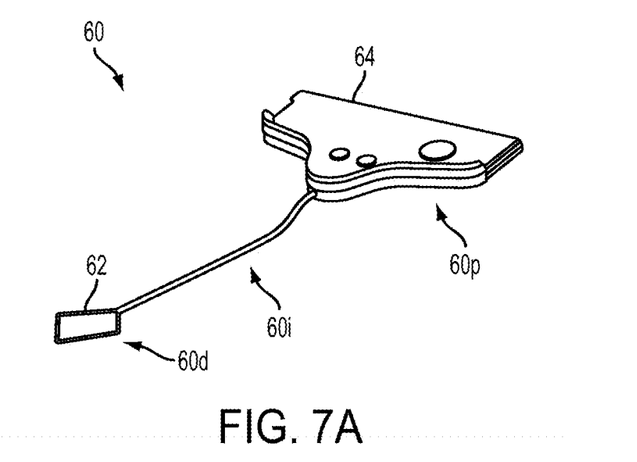
FIG. 7A is a perspective view of a suture filament threader of the device of FIG. 1A.
Figure 7B:
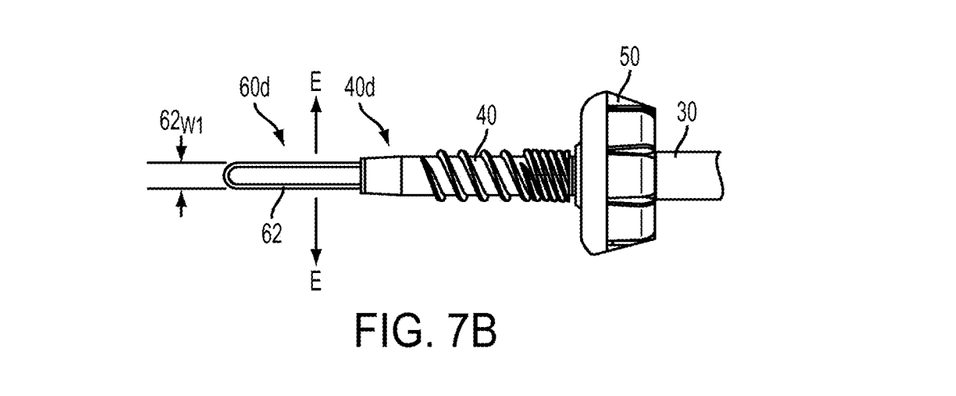
FIG. 7B is a top view of a distal end of the threader of FIG. 7A in a compressed form.
Figure 7C:
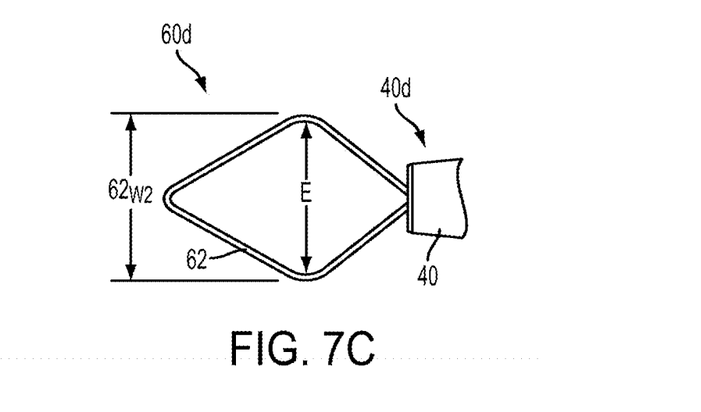
FIG. 7C is a top view of the distal end of the threader of FIG. 7B in an expanded form.

The threader 60 illustrated in FIG. 7A generally includes a distal end 60d having an opening 62 to receive suture filament to be loaded onto an anchor, a proximal end 60p having a handle 64, and a flexible intermediate portion 60i disposed therebetween. As illustrated in FIGS. 7B and 7C, the distal end 60d can be flexible, thereby allowing an opening 62 thereof to move between multiple configurations. In one configuration, shown in FIG. 7B and referred to herein as a compressed or starting configuration, the opening 62 has an elongate shape with a substantially uniform width $62_{W1}$. The distal end 60d can be packaged in this starting configuration. As a result, once the threader 60 is removed from the packaging, it can be passed through the ring 50 and the anchor 40 without any manipulation of the distal end 60d. As shown in FIG. 7B, the distal end 60d can then be adjacent to a distal end 40d of the anchor 40 prior to associating any operative filament with the anchor 40.

The distal end 60d can then be moved to a second configuration, shown in FIG. 7C and referred to herein as an open configuration. While the open configuration can have any number of shapes, as shown the opening 62 is substantially diamond-shaped, thereby creating an opening having a wider width $62_{W2}$ through which operative filament can be looped to be subsequently passed through the anchor 40. The opening 62 can be moved from the compressed configuration to the open configuration by applying outward forces in a direction E to ends 60e of the distal end 60d, for instance by placing a pliers-like instrument within the opening 62 and opening the instrument to apply the outward force.

The handle 64 of the threader 60 can have any shape, and can generally be configured to allow a surgeon to easily grasp and pull the distal end 60d and intermediate portion 60i toward the handle 20 of the tool 10. As the distal end 60d advances proximally, the opening 62 can become compressed so that it can pass through the anchor 40. The intermediate portion 60i can generally be flexible, but can have a substantially fixed length so that tension forms therein when pulling the distal end 60d through the anchor 40. In some embodiments the intermediate portion 60i can extend through the third chamber 46 of the distal end 30 of the shaft 30 prior to passing the suture filament through the anchor 40. As a result, operative suture pulled through the anchor 40 by the threader 60 can be disposed through the third chamber 46.

Shapes, sizes, and materials used to form the threader 60 are commensurate with other components of the device 10 and are known to those skilled in the art. Notably, because the threader 60 can be shorter than in previously known anchor insertion devices, a length of the intermediate portion 60i can be smaller than in previous devices. In some embodiments a length of the intermediate portion 60i can be in the range of about 1 centimeter to 10 centimeters, and in one embodiment it can be about 3.9 centimeters. In one exemplary embodiment the distal end 60d is made of a wire, the intermediate portion 60i is made of a flexible filament, and the proximal portion 60p is made of a plastic material. A person skilled in the art will also recognize that other devices known for associating or coupling a suture filament with anchors can also be used instead of a threader.

In use, the anchor insertion device 10 can be used to implant one or more anchors at a surgical location. FIGS. 8A-8D illustrate one exemplary embodiment of a procedure for implanting a suture anchor 40 at a surgical site. A surgical opening can be formed through skin 2 and a trocar 100 can be passed therethrough to provide a portal through tissue to the surgical site. As shown, the trocar 100 can extend proximally from the skin 2 and can include a port 102 through which surgical instruments are inserted to access the surgical site. The port 102 is disposed proximal of a valve 104 configured to insufflate the surgical site. In some embodiments, a pre-formed hole can be formed in bone, in which the anchor 40 will ultimately be disposed. The hole can be formed using any technique known to those skilled in the art, including, by way of non-limiting example, by using a surgical awl.

Figure 8A:
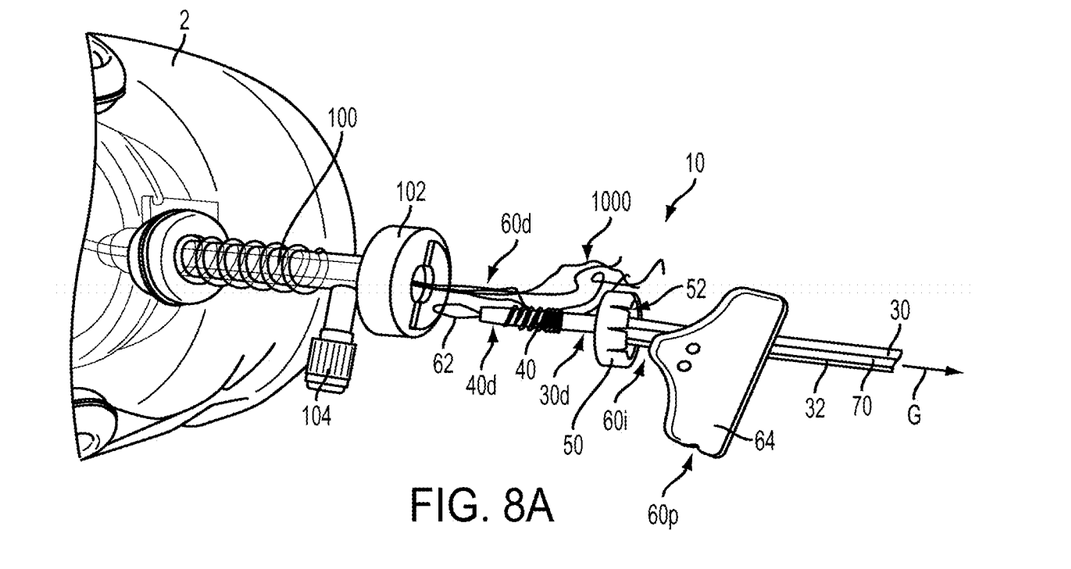
FIGS. 8A-8D are sequential schematic views illustrating one exemplary embodiment for using the device of FIG. 1A in a surgical procedure.

One or more surgical filaments 1000 for use in repairing tissue can be inserted through the trocar 100 and to the surgical site, with ends of the surgical filaments extending back through the trocar 100 and out of the port 102, as shown in FIG. 8A. The ends extending out of the port 102 can be used by the surgeon to perform the tissue repair. Many different techniques can be used to dispose the surgical filaments 1000 at the surgical site. In some embodiments, one or more of the filaments 1000 can be coupled to a needle and the needle passed through tissue to couple the one or more filaments 1000 to tissue. In other embodiments one or more of the filaments 1000 can be wrapped around tissue to be repaired. In still other embodiments, one or more of the filament 1000 can be attached to implantable bone anchors and the anchors can be driven into bone at or near the surgical site so that the one or more filaments 1000 are at the surgical site for subsequent use. In such embodiments one or more of the filaments 1000 can still be coupled to the tissue to be repaired.

To the extent components of the assembly are not already set-up for use in the surgical procedure, the surgeon can set-up the assembly for use in the tissue repair. The shaft 30 can be coupled to the handle 20 (shown in FIG. 8C), the ring 50 can be disposed around the shaft 30, the anchor 40 can be coupled to distal end 30d of the shaft 30 and held in place by the stay suture 70, and the threader 60 can be associated with the anchor 40 and shaft 30. More particularly, the distal end 60d and intermediate portion 60i of the threader can be inserted through the central opening 52 of the ring 50, through a portion of the slot 32 of the elongate shaft 30, and through the anchor 40 such that the opening 62 of the distal end 60d is distal of and adjacent to the distal end 40d of the anchor 40, the handle 64 of the proximal end 60p is proximal of and adjacent to the ring 50, and the intermediate portion 60i extends therebetween. One or more of the filaments 1000 extending from the port 102 can be looped through the opening 62 of the threader 60 for subsequent passing through the cannulated anchor 40.

Figure 8B:
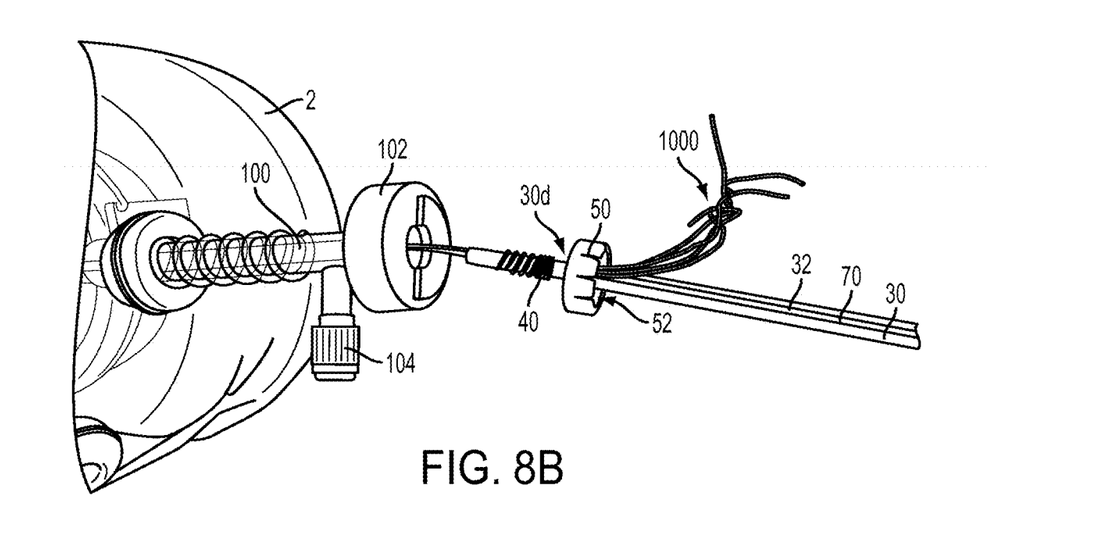

The one or more filaments 1000 can be passed through the anchor 40 by pulling the threader handle 64 in an approximately proximal direction G. This action causes the intermediate portion 60i to become tensioned and the intermediate portion 60i and distal end 60d to advance proximally through the anchor 40. The opening 62 of the distal end 60d can collapse to pass through the anchor 40, and as it passes through the anchor 40, so do portions of the filament(s) 1000 coupled thereto. The opening 62 can be passed to a proximal side of the ring 50, and the filament(s) 1000 coupled thereto can be decoupled from the threader 60 and the threader 60 removed from the assembly. As shown in FIG. 8B, the resulting configuration can be one in which ends of filaments 1000 extend out of the port 102, through the anchor 40, at least a portion of the shaft 30, the ring central opening 52, and out at least to a location proximal of the ring 50 for subsequent use in a surgical repair procedure. The filaments 1000 extending distal of the port 102 can remain disposed in the body as the threader 60 is pulled proximally because of counteracting forces in the body. These counteracting forces can be provided, by way of non-limiting example, by having the respective filaments 1000 coupled to tissue in the body or being anchored in bone prior to operating the threader 60.

Figure 8C:
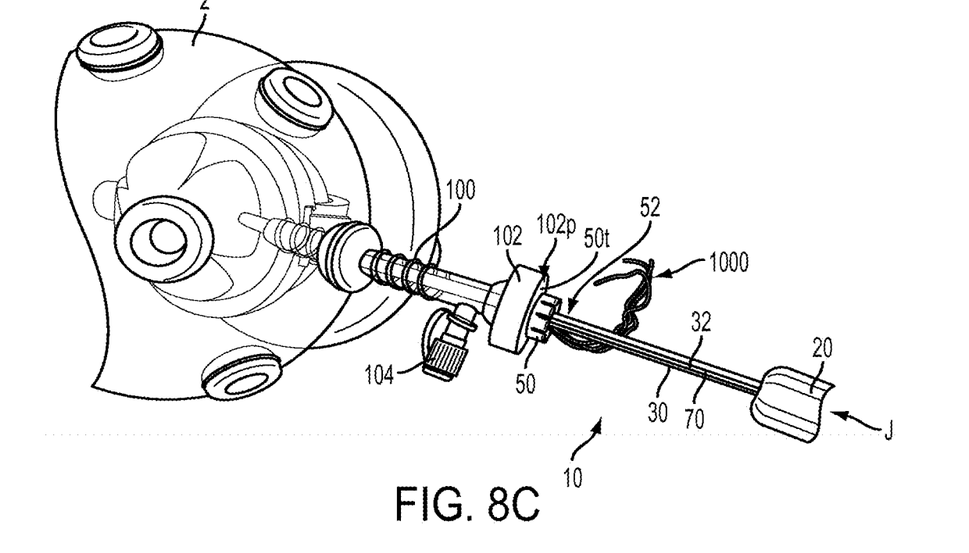

The anchor 40 can be advanced toward the surgical site, as shown in FIG. 8C. A force in an approximate direction J can be applied to the inserter shaft 30, thus causing the anchor 40 to advance in the direction J. As the shaft 30 and anchor 40 advance distally, the ring 50 can slide with respect to shaft 30 such that a distance between the distal end 30d of the shaft 30 and ring 50 increases. In one embodiment, the anchor 40 is advanced distally to the surgical site to a location that is proximate to the bone to which tissue is to be attached, but the anchor 40 is not inserted into the pre-formed bone hole. As shown, during insertion of the shaft 30 and anchor 40, a distal surface 50t of the ring 50 can be disposed adjacent to a proximal surface 102p of the port 102. Further, because in the illustrated embodiment the boss (not shown) formed on the circumference of the central opening 52 is disposed in the slot 32 of the shaft 30, the ring 50 does not rotate as it slides with respect to the shaft 30. Still further, the ends of the filaments 1000 extending out of the port 102 can be grasped by the user to help prevent them from advancing distally below the port 102 with the anchor 40. The surgeon can grasp the filaments 1000 near the port 102 because the length of the filaments 1000 extending out of the port 102 can be substantially shorter than previous tissue repair assemblies. This makes it easier for a surgeon to manage the filaments 1000 and related components of the assembly.

Figure 8D:
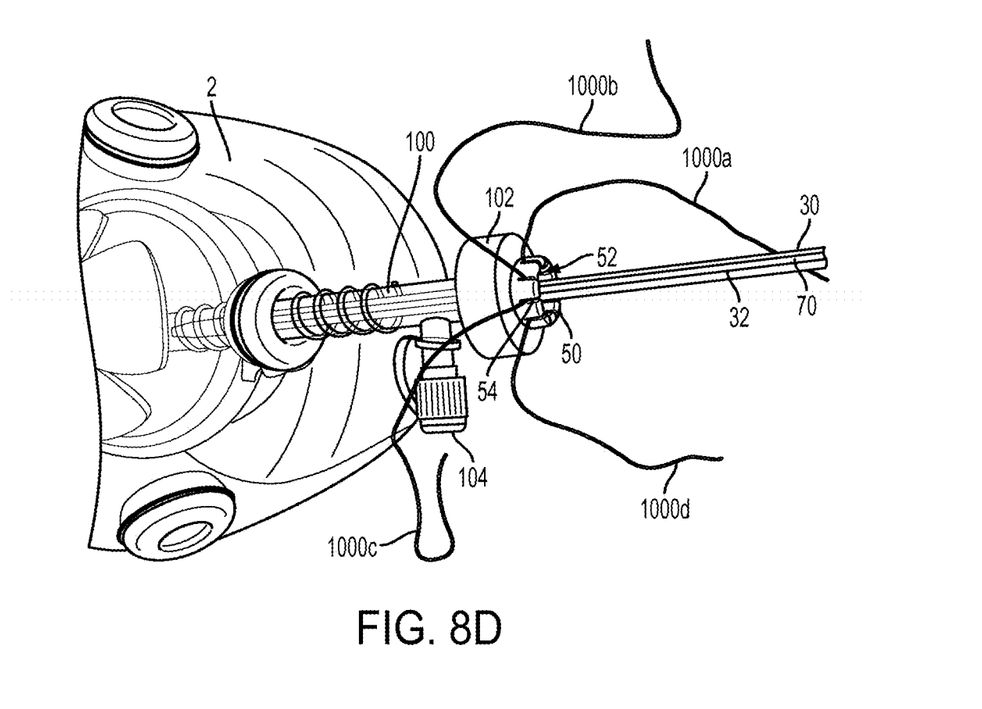

The ends of the filaments 1000 extending from the body and out of the ring 50 can be manipulated to perform a number of different surgical procedures. A person skilled in the art will recognize many different ways the filaments 1000 can be manipulated. By way of non-limiting example, manipulation can include moving one or more of the filaments 1000 axially to adjust a location of the respective filaments 1000 and any tissue attached thereto. By way of further non-limiting example, manipulation can include applying tension to one or more of the filaments 1000 to draw tissue coupled thereto towards a desired location, such as bone. As strands of the filaments 1000 are manipulated to desired locations, the desired location and/or the desired amount of tension applied thereto can be maintained by disposing the strands in slots 54 formed in the ring 50. As shown in FIG. 8D, each end 1000*a*, 1000*b*, 1000*c*, 1000*d* of filaments 1000 can be tensioned to a desired amount and/or otherwise manipulated to a desired location and can be disposed in separate slots 54 of the ring 50. Alternatively, multiple strands of suture filaments can be disposed in the same slot 54 if desired.

In one exemplary embodiment, after all filaments 1000 have been manipulated and otherwise tensioned as desired, the filaments 1000 can be removed from the slots 54 and grasped by the surgeon. The surgeon can then insert the anchor 40 into the pre-formed hole in bone, for example by rotating the tool 10 to twist the anchor 40 into the pre-formed hole. Other techniques for inserting suture anchors into bone can also be used. The resulting interference between the hole and the anchor 40 can maintain a location of the filaments 1000, and thus the tissue coupled thereto, with respect to the bone. Further, as the tool 10 is rotated, the ring 50 can engage the filaments 1000 to prevent them from undesirably wrapping around portions of the shaft 30, particularly portions located distal of the port 102.

After the anchor 40 is implanted, the stay suture 70 can be removed. This can occur by opening the door 22 (not shown) of the handle 20 (not shown), disassociating ends 70*a*, 70*b* (not shown) of the stay suture 70 from the posts 25 (not shown), gripper 90 (not shown) and card 80 (not shown), and pulling the stay suture 70 out of communication with the rest of the device 10. As a result, the shaft 30 can be separated from the anchor 40, and the shaft 30 can be removed from the surgical site. As the shaft 30 is removed from the surgical site, the filaments 1000 extending through the ring central opening 52 can be engaged and guided by the ring 50 to reduce the possibility of any unwanted twisting of the filaments 1000 around the shaft 30. After the shaft 30 is removed, final manipulation of the filaments 1000 can occur to secure a location of the tissue with respect to the bone. Final manipulation can include actions such as tying a knot, cutting the filament, or other manipulations known to those skilled in the art.

One skilled in the art will appreciate further features and advantages of the invention based on the above-described embodiments. Accordingly, the invention is not to be limited by what has been particularly shown and described, except as indicated by the appended claims. By way of non-limiting example, a person skilled in the art will recognize other surgical procedures involving suture filaments with which the tool 10, and components thereof, including the ring 50, can be used in view of the disclosures herein. All publications and references cited herein are expressly incorporated herein by reference in their entirety.

What is claimed is:

1. A method for repairing tissue, comprising:
inserting a suture anchor removably and replaceably coupled to a distal end of an inserter shaft through a cannula to position the suture anchor adjacent to an implant site, the suture anchor having a suture filament associated therewith that extends proximally from the anchor and through the inserter shaft, and the inserter shaft having a ring slidably disposed therearound and coupled to the suture filament such that the ring and the inserter shaft are simultaneously distally advanced towards the cannula as the anchor moves toward the implant site,
wherein advancement of the inserter shaft through the cannula causes the ring to slide relative to the inserter shaft while a distance between the anchor and the ring increases.

2. The method of claim 1, wherein as the anchor moves toward the implant site, the ring abuts a face of the cannula.

3. The method of claim 1, further comprising inserting the suture filament into a slot of the ring to maintain a tension applied to the suture filament.

4. The method of claim 1, further comprising rotating the inserter shaft to insert the suture anchor into bone while the ring guides a trailing portion of the suture filament through a slot formed in the inserter shaft.

5. The method of claim 1, further comprising:
decoupling the suture anchor from the inserter shaft; and
removing the inserter shaft from the implant site, the ring guiding a trailing portion of the suture filament through a slot formed in the inserter shaft as the inserter shaft is removed.

6. The method of claim 5, wherein decoupling the suture anchor from the inserter shaft further comprises releasing a second suture filament extending distally from a handle and to a distal end of the anchor.

7. The method of claim 1, further comprising:
loading a suture filament onto a distal portion of a threader that is located distal of the suture anchor, the threader having an intermediate portion extending through the suture anchor and a proximal portion located proximal of the suture anchor, the proximal portion being disposed adjacent to the ring; and
pulling the proximal portion of the threader proximally along the shaft, away from the ring, to advance the distal portion of the threader, and thus the suture filament loaded thereon, through the suture anchor and through the ring.

* * * * *